United States Patent [19]

Rietzel et al.

[11] Patent Number: 4,910,203
[45] Date of Patent: Mar. 20, 1990

[54] PTERIDINE COMPOUNDS

[76] Inventors: Christian Rietzel, Wilckensstrasse 22, Heidelberg; Heinrich Knauf, Birkwaeldele 28, Freiburg-Wittnau; Ernst Mutschler, Am Hechenberg 24, Mainz-Hechtsheim; Karl-Dieter Voelger, Bebelstrasse 10, Bickenbach, all of Fed. Rep. of Germany

[21] Appl. No.: 185,319

[22] Filed: Apr. 20, 1988

Related U.S. Application Data

[63] Continuation of Ser. No. 883,459, Jul. 9, 1986, abandoned, which is a continuation of Ser. No. 703,801, Feb. 21, 1985, abandoned.

[30] Foreign Application Priority Data

Mar. 2, 1984 [DE] Fed. Rep. of Germany ....... 3407695

[51] Int. Cl.[4] .................. A61K 31/495; C07D 475/08
[52] U.S. Cl. .................... 514/258; 544/260; 544/118; 514/234.2
[58] Field of Search .......... 514/258; 544/260

[56] References Cited

U.S. PATENT DOCUMENTS

| | | | |
|---|---|---|---|
| 3,081,230 | 3/1963 | Weinstock et al. | 544/260 |
| 4,252,809 | 2/1981 | Knauf | 544/260 |
| 4,285,947 | 8/1981 | Higuchi | 544/260 |
| 4,327,113 | 4/1982 | Smith | 260/465 E |

FOREIGN PATENT DOCUMENTS

| | | | |
|---|---|---|---|
| 1597881 | 9/1981 | United Kingdom | 544/260 |
| 1597882 | 9/1981 | United Kingdom | 544/260 |

OTHER PUBLICATIONS

Kraft Chemical Abstracts 103:16326s (1985).
Priewer Chemical Abstracts 103:31950j (1985).

March "Advanced Organic Chemistry" 2nd Edition (1977), p. 381.
Houben-Weyl, Methoden der Organischen Chemie, 4th Ed., vol. VII, Part I ("Aldehydes"), pp. 414–416.
Karrer, Lehrbuch der Organischen Chemie, 13th Ed., p. 352.
Charton et al., Steric Effects in Drug Design, p. 9.
Kirk–Othmer, Encyclopedia of Chemical Technology, 3rd Ed., vol. 17, pp. 350–351.

*Primary Examiner*—Sam Rosen
*Assistant Examiner*—Robert Benson

[57] ABSTRACT

Pteridine compounds, useful as diuretics, of the formula

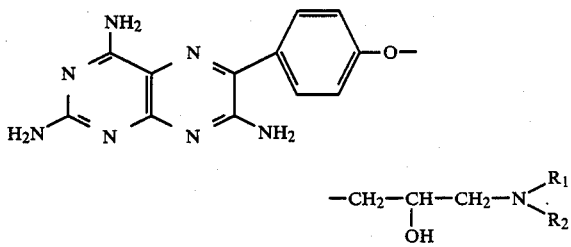

wherein $R_1$ and $R_2$ taken alone are, independently of each other, hydrogen, alkyl having from 1 to 6 carbon atoms, or benzyl, or wherein $R_1$ and $R_2$, taken together with the nitrogen atom to which they are bound, form a five- or six-membered heterocyclic ring system or such a ring containing one or two further hetero atoms, or wherein $R_1$ and $R_2$ together with the nitrogen are

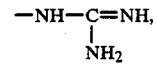

11 Claims, No Drawings

PTERIDINE COMPOUNDS

This application is a continuation of application Ser. No. 883459, filed on July 9, 1986, now abandoned, which in turn is a continuation of Ser. No. 703801, filed Feb. 21, 1985, now abandoned.

The present invention relates to certain pteridine compounds, i.e. to derivatives of triamterene (2,4,7-triamino-6-phenyl- pteridine), having diuretic, antikaliuretic, calcium- antagonistic, and cardioprotective activity, and to a method of making and using the same.

British patent No. 1,597,881 discloses diuretically active derivatives of triamterene in which the para position of the 6-phenyl ring is etherified with a hydrophilic group. The concept so disclosed is at variance with the work of Weinstock et al. (J. Med. Chem. 11, 573 [1968]), according to which the diuretic action of triamterene derivatives is enhanced by lipophilic substitution, whereas hydrophilically substituted derivatives are not likely to possess diuretic activity. The British patent cited names a number of compounds which support the diuretic activity of such hydrophilically substituted compounds. However, many parameters enter into the profile of an active ingredient, for example, activity, acute and chronic toxicity, compatibility with other active substances, pharmacokinetics and pharmacodynamics, metabolism, and physical and chemical parameters such as stability, solubility, availability, etc.

The general formula of the compounds of British patent No. 1,597,881 also includes derivatives with basically substituted groups, and such groups are also described. In the course of subsequent further scientific investigations of this class of compounds, however, hydroxytriamterene ethers with alcoholic or acidic groups were held to be particularly promising. See H. Knauf et al., Therapiewoche 30, 6831-6847 (1980). There it is stated, inter alia: "From the results mentioned, it can be concluded that the goal of obtaining an effective, water soluble triamterene derivative with good pharmacokinetic properties can be attained by retaining the basic triamterene structure and introducing into it a suitable side chain with a carboxyl group which will impart amphiphilic properties to the molecule." Further: "It can thus be said that it has proved possible to obtain the desired quick acting, water soluble triamterene derivatives."

Hydroxytriamterene ethers having acidic functions, and particularly 2,4,7-triamino-6-[4-(4-carboxybutoxy)-phenyl]-pteridine (hereinafter abbreviated as Val-O-TA) exhibit diuretic, natriuretic, and antikaliuretic activity when administered intravenously. The kaliuresis produced by furosemide, for example, can be compensated practically fully with Val-O-TA.

However, when administered perorally to rats in amounts of about 50 mg/kg body weight, he acid derivatives exhibit no promising diuretic action. The solubilities of the straight chain acid derivatives are of the order of 0.1 percent in the range from pH 11 to 12.

Thus, there has been a need for finding an active substance whose properties would preferably impose no restrictions on the modes of administration and whose pharmacological properties would be at least as good as those of triamterene. Moreover, its metabolism should not give rise to new problems. What has been sought in particular is an active substance of relatively good water solubility that would readily lend itself to intravenous administration. Such an active substance would be suitable as a partner in combination therapy with the quick acting diuretic furosemide, if indicated by the pharmacokinetic and pharmacodynamic parameters.

It has been found that this need is filled by pteridine compounds of the formula

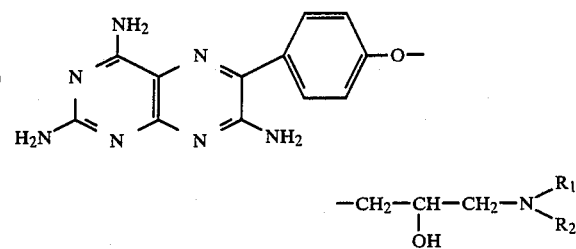

wherein $R_1$ and $R_2$ are, independently of each other, hydrogen, linear or branched alkyl having from 1 to 6 carbon atoms, or benzyl, or wherein $R_1$ and $R_2$, taken together with the nitrogen atom to which they are bound form a five- or six-membered heterocyclic ring system which may include one or two further hereto atoms, primarily nitrogen and oxygen, but also sulfur, or wherein $R_1$ and $R_2$ together with the nitrogen atom to which they are bound are

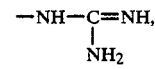

and by the pharmaceutically acceptable acid addition salts of such compounds.

The compounds of the formula have a chiral center. The present claims are intended to include all forms which can be distinguished with respect to chirality.

Pharmaceutically acceptable acid addition salts within the meaning of the present invention are those with inorganic acid radicals, for example the chlorides, bromides, sulfates, carbonates, and phosphates, or with organic carboxylic or sulfonic acid radicals, for example salts of acetic acid, propionic acid, oxalic acid, malonic acid, succinic acid, fumaric acid, maleic acid, lactic acid, tartaric acid, malic acid, citric acid, benzoic acid, methane- or ethane-sulfonic acid, and of ethanedisulfonic acid. Of the salts, the tartrates, and especially the hydrogen tartrates, are preferred.

The compound of the formula and the acid addition salts derived therefrom may be prepared by prior art methods, for example, by the procedure employed by R. G. W. Spickett and G. M. Timmis (J. Chem. Soc., 2887-95 [1954]) or in British patent No. 1,397,881.

This is advantageously done by reacting a substituted benzyl cyanide of the formula

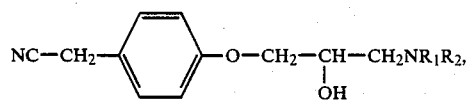

wherein $R_1$ and $R_2$ have the same meanings as before, base catalyzed with 2,4,6-triamino-5-nitroso-pyrimidine, to give the desired compounds. The reaction can be carried out with an alkali metal alcoholate as the base and the corresponding alcohol as a solvent, with exclusion of moisture, in a suitable vessel equipped with a condenser and stirrer. Suitable alcohols include alkoxyalkanols such as ethoxyethanol. The alkoxide is advantageously produced in the apparatus from alcohol and alkali metal under a dry protective gas. The 2,4,6-triamino-5-nitrosopyrimidine and the starting benzyl cyanide compound are preferably introduced in slight excess, optionally followed by rinsing with the alcohol. The reaction is allowed to proceed for some time, for example 2 hours, with stirring and preferably at elevated temperature, for example with reflux, and the reaction mixture is then allowed to cool, for example overnight. The precipitate formed is filtered off, washed with a suitable solvent such as acetone, and advantageously dried for some time in a drying chamber, preferably with heating and under vacuum. If desired, the compounds may be further purified, for example by recrystallization from 1 N hydrochloric acid, in which case dihydrochlorides are then obtained.

The conversion of the desired basic compounds to the corresponding acid addition salts can generally be carried out conventionally by reaction with the corresponding acid.

The aforementioned substituted benzyl cyanides are in turn advantageously prepared by the addition of an amine of the formula

wherein $R_1$ and $R_2$ have the same meanings as before, to the epoxy group of 3-(4-cyanomethylphenoxy)propylene oxide.

Advantageously, the amines are added in an excess (guide value, about fivefold for secondary amines and tenfold for primary amines) to a solution of the epoxy compound in an alcohol. A portion of the amine may also be used in the form of an aqueous solution, for example a 40 percent solution. It is advisable to use the secondary amines in an anhydrous medium, for example an alcohol such as methanol. Amines with some steric hindrance, for example diisopropylamine, are best heated, for example by refluxing.

The yields will generally be at least 50 percent and up to 95 percent.

3-(4-cyanomethylphenoxy)propylene oxide may be prepared conventionally, for example by reacting 4-hydroxy-benzyl cyanide with epibromo- or epichlorohydrin.

The following compounds are among those to which this application is directed:

2,4,7-Triamino-6-[4-(2-hydroxy-3-aminopropoxy)-phenyl]pteridine 2,4,7-Triamino-6-[4-(2-hydroxy-3-methylaminopropoxy)phenyl]-pteridine 2,4,7-Triamino-6-[4-(2-hydroxy-3-dimethylaminopropoxy)phenyl]-pteridine 2,4,7-Triamino-6-[4-(2-hydroxy-3-ethylaminopropoxy)phenyl]-pteridine 2,4,7-Triamino-6-[4-(2-hydroxy-3-diethylaminopropoxy)phenyl]-pteridine 2,4,7-Triamino-6-[4-(2-hydroxy-3-propylaminopropoxy)phenyl]-pteridine 2,4,7-Triamino-6-[4-(2-hydroxy-3-dipropylaminopropoxy)phenyl]-pteridine 2,4,7-Triamino-6-[4-(2-hydroxy-3-isopropylaminopropoxy) phenyl]-pteridine 2,4,7-Triamino-6-[4-(2-hydroxy-3-diisopropylaminopropoxy)phenyl]-pteridine 2,4,7-Triamino-6-[4-(2-hydroxy-3-n-butylaminopropoxy)phenyl]-pteridine 2,4,7-Triamino-6-[4-(2-hydroxy-3-di-n-butylaminopropoxy)phenyl]-pteridine 2,4,7-Triamino-6-[4-(2-hydroxy-5-morpholinopropoxy)phenyl]-pteridine 2,4,7-Triamino-6-[4-(2-hydroxy-3-piperidinopropoxy)phenyl]-pteridine 2,4,7-Triamino-6-[4-(2-hydroxy-3-pyrrolidinopropoxy)phenyl]-pteridine 2,4,7-Triamino-6-[4-(2-hydroxy-3-N-methyl-piperazinopropoxy)phenyl]-pteridine 2,4,7-Triamino-6-[4-(2-hydroxy-3-benzylaminopropoxy)phenyl]-pteridine as well as the acid addition salts derived from these compounds, and particularly the bis-hydrochlorides.

The compounds of the invention and the acid addition salts derived therefrom are yellowish, crystalline compounds which in ultraviolet light exhibit the strong fluorescence typical of pteridine compounds.

They are surprisingly easily soluble in water, especially at pH values of under 7. The acid addition salts are also readily soluble.

The compounds and their addition salts with pharmaceutically acceptable acids are well suited for oral and intravenous administration.

The diuresis tests reported herein below were carried out by the following procedures:

Diuresis tests: Procedures

For the tests, male Wistar rats of about 130 g body weight from which food had been withheld for 18 hours were used. They were orally given 20 ml/kg of an 0.9% NaCl solution just before the test substance was administered intravenously. Intravenous administration for determining $K^+$ was at dosage intervals for the actiee substance of 0.05, 0.1, 0.2, 0.3, 0.6, 1, and 2 mg/kg: for determining $Na^+$ at dosage intervals of 0.5, 1, 2, 4, 8, 16 and 20 mg/kg. For the prior art substances compared, the same tests were made and these substances were further administered at 30 mg/kg and 100 mg/kg. Injection was into the caudal vein under light etherization. As a rule, six test animals were used per test. Peroral administration was by means of a stomach tube into the gastrointestinal tract. The animals were individually placed into diuresis cages and the urine was collected after 2.5 hours.

The electrolytes ($Na^+/K^+, Mg^{+2}$) were determined by flame photometry and by atom absorption spectrophotometry with an FL6 automatic electrolyte measuring device manufactured by Zeiss, Oberkochen.

Dose response curves were constructed by the use of non-linear regression analysis using the NONLIN computer program of C. Daniel and F. S. Wood in "Fitting Equations to Data" (J. Wiley & Sons, New York, 1980).

The characteristic quantity $ED_{50}$ (potency) used in determining the diuretic activity is defined as the amount of active substance per kilogram of body weight required to produce a response in 50 percent of the subjects.

The following data illustrate the superior efficacy of a typical compound of the invention, (2,4,7-triamino-6-[4-(2-hydroxy-3-dimethylaminopropoxy) phenyl]-pteridine), hereinafter called "Inventive Compound" in comparison with triamterene and 2,4,7-triamino-6-[4-(3-dimethylaminopropoxy)phenyl]-pteridine (=DES—OH).

| Active substance | ED$_{50}$ (micromoles per kilogram) of body weight | | |
|---|---|---|---|
| | Na$^+$ | K$^+$ | Mg$^{+2}$ |
| Triamterene | 4.40 | 1.87 | — |
| DES-OH | 5.53 | 0.54 | — |
| Inventive Compound | 9.36 | 0.24 | 0.40 |

The compound of the invention exhibits outstanding diuretic efficacy with respect to both its natriuretic and its potassium- and magnesium-sparing properties.

In this respect, it is definitely superior to triamterene and to the desoxy compound. The potassium-sparing effect sets in at one-tenth of the dosage at which triamterene becomes effective.

Based on the investigative data at hand, the substituent influence of the —NR$_1$R$_2$ group on the potency of the compounds of the invention exhibits approximately the following pattern:

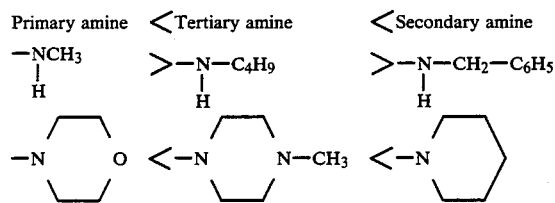

The toxicity values with intravenous administration, for example, are good. The good elimination observed on intravenous administration is also of practical importance.

Based on the investigations carried out so far, the compounds (and their salts) of the invention are not metabolized.

Their high potency permits relatively low dosage of the inventive compounds. However, of course, the weight, age, constitution, and general state of health of the patient must be taken into consideration. A daily dose of from 0.2 to 100 mg, and preferably from 1.5 to 20 mg, will usually be aprropriate. As a guide value, from 0.02 to 10 mg/day may be administered per kilogram of body weight. It may be administered in several dosage units, for example 2 four times daily. Administration may be oral or parenteral. For oral administration, daily doses are in general in the range from 0.15 to 1.5 mg per kilogram of body weight, for intravenous administration, daily doses from 0.02 to 0.8 mg per kilogram of body weight, prefrably 0.05 to 0.4 mg, and particularly 0.1 to 0.2 mg per kilogram of body weight, are recommended.

The substances of the invention are highly suitable for use as pharmaceuticals having diuretic, antikaliuretic, antimagnesiuretic, antihypertensive, and cardioprotective action. Moreover, they lend themselves well to combination with other active substances having comparable indications and with which they are compatible. Of considerable importance i their combination with quick acting diuretics such as furosemide (4-chloro-N-furfuryl-5-sulfamoylanthranilic acid, according to U.S. Pat. No. 3,058,882).

It should be noted that the kaliuretic action of furosemide can be compensated for with about one-tenth the dose of a compound of the invention. The ratio of the amounts to be administered generally ranges from 0.25 to 100 parts by weight of furosemide to 1 part by weight of the compound of the invention. With a recommended daily dose of 2×40 mg peroral furosemide, the administration of 8 mg of the inventive compound is indicated. Intravenous administration of 20±5 mg of furosemide corresponds with the intravenous administration of 2 to 8 mg of the active substance of the invention.

Combination of the invention with a calcium-antagonistic active substance, as are also used in published German patent application DOS Nos. 26 58 500 for example, and particularly Verapamil, Gallopamil, Nifedipin, and Diltiazem, is also of special interest. The weight ratio of the calcium antagonist to the active substance of the invention in such combination preparations may range from 100:1 to 0.1:1.

Combination of the potassium-sparing ative substances of the invention with other diuretics is also of considerable interest. (See Ullmanns Enzyklopadie der technischen Chemie, 4th ed., vol. 10, pp. 181–186, Verlag Chemie, 1975.) Illustrative of these are the saluretics, and particularly benzothiadiazine derivatives such as chlorothiazide, hydrochlorothiazide, and the analogs of hydrochlorothiazide, and especially hydroflumethiazide, thiabutazide, bendroflumethiazide, trichloromethiazide, methylcyclothiazide, polythiazide, cyclothiazide, cyclopenthiazide, ethiazide, benzthiazide, and methylbenzylhydrochlorothiazide, as well as sulfamoyl saluretics such as Chlorthalidon, Mefrusid, Clopamid, Quinethazon, and Chlorexolon.

In such combinations, the weight ratio of the active substances of the invention to the dose recommended for each of the prior individual diuretic agents may then range from 2:1 to 0.01:1.

Specifically, in combination with hydrochlorothiazide the weight ratio between the substance of the invention and the saluretic may range from 1:1 to 0.05:1.

The compounds of the invention are also suitable for combination with beta blockers in the manner of the combination preparations with triamterene taught in British patent No. 1,584,089, and especially for combination with propaanolol or its acid addition salts. The combination may further contain saluretics.

The weight ratio of the active substances of the invention to the beta blockers may then range from 2:D to 10:D, D being the recommended aily dose or down to one-half the recommended daily dose.

The pharmaceutical preparations incorporating the new compounds of the invention may be produced in the usual manner and may contain commonly used carriers and adjuvants. One embodiment of the invention consists of solid preparations suitable for oral administration, for example tablets, capsules, dragees, etc. For oral administration, pharmaceutically inactive solids such as manniol, lactose, organic and inorganic calcium salts, etc., may be used as carriers. Suitable binders include polyvinylpyrrolidone, gelatin, or cellulose derivatives. Tablet disintegrants such as starch or alginic acid, lubrcants such as stearic acid or its salts, inorganic flow promoters such as talc or silica gel, and taste masking agents, etc., may be used as further additives.

The active substances can be mixed with the auxiliary materials in the usual manner and granulated wet or dry. Depending on the type of additive used, it may be possible to obtain by simple mixing a powder which can be compressed directly into tablets. The granules or powder may be filled directly into capsules or compressed coventionally into tablet cores.

For parenteral use, the therapetttic agents may also be prepared and administered in the usual manner.

The Examples which follow will serve to illustrate the preparation of the compounds of the invention and the production of pharmaceutical preparatioss containing the same.

Among the analytical methods employed in the Examples was thin-lyer chromatography on precoated plates (Merck, silica gel 60, F 254, article No. 5715) in various solvents.

| Solvent 1: | Ethyl acetate/methanol/NH₃ (25%) | 60:30:10 (v/v) |
|---|---|---|
| Solvent 2: | " | 70:20:10 |
| Solvent 3: | " | 80:20:10 |
| Solvent 4: | " | 35:55:10 |
| Solvent 5: | Methanol/NH₃ (25%) | 90:10 |
| Solvent 6: | N-butanol/methanol/chloroform/NH₃ (25%) | 50:15:15:15 |

EXAMPLE 1

2,4,7-triamino-6-[4-(2-hydroxy-3-dimethylaminopropoxy) phenyl]-pteridine (Designation: IA)

Reaction mixture: 45.0 g (192 millimoles) of 1-(4-cyanomethylphenoxy)-3-dimethylamino-2-propanol, 27.1 g (176 millimoles) of 2,4,6-triamino-5-nitrosopyrimidine (TPP), 4.1 g (176 millimoles) of sodium, and 1125 ml of 2-ethoxyethanol.

925 ml of 2-ethoxyethanol were charged into a 2-liter round-bottom three-necked flask equipped with magnetic stirrer, condenser, drying tube (with $CaCl_2$ filling), and thermometer and the apparatus was flushed with argon for 10 minutes. 4.1 g of sodium were then added to the ethoxyethanol. After all the sodium had dissolved, 27.1 g of 2,4,6-triamino-5-nitrosopyrimidine and 45.0 g of 1-(4-cyanomethylphenoxy)-3-dimethylamino-2-propanol were introduced into the reaction flask and blanketed with 200 ml of 2-ethoxyethanol. The reaction mixture was refluxed for 2 hours and then allowed to cool to room temperature overnight. The precipitate formed was filtered off by suction through a D-4 glass filter, washed with a total of 1 liter of acetone, and dried for 14 hours at 60° C. in a vacuum oven (oil-pump vacuum).

Yield: 34.5 g (53.0% of theory).

Retention factor ($R_f$) (solvent 1): 0.40.

Other compounds of the invention listed below in Table 1 can be prepared by the same procedure used in Example 1.

TABLE 1

| Example No. | Designation | Pteridine compound $-N\begin{smallmatrix}R_1\\R_2\end{smallmatrix}$ | Form of salt | | Elementary analysis C H N Cl | Solvent No. | $R_f$ |
|---|---|---|---|---|---|---|---|
| 3 | IB | $-N\begin{smallmatrix}H\\C_2H_5\end{smallmatrix}$ | 2HCl H₂O | Calc. Found | 44.3% 5.7% 24.3% 15.4%<br>44.3% 6.4% 24.0% 15.1% | 6 | 0.36 |
| 4 | IC | $-N\begin{smallmatrix}H\\CH_3\end{smallmatrix}$ | 2HCl H₂O | Calc. Found | 43.0% 5.4% 25.1% 15.9%<br>43.0% 6.2% 24.7% 15.8% | 6 | 0.31 |
| 5 | ID | $-N\bigcirc O$ (morpholino) | 2HCl H₂O | Calc. Found | 45.3% 5.6% 22.3% 14.1%<br>45.1% 6.0% 22.2% 14.1% | 6 | 0.50 |
| 6 | IE | $-N\begin{smallmatrix}C_2H_5\\C_2H_5\end{smallmatrix}$ | 2HCl H₂O | Calc. Found | 46.6% 6.2% 22.9% 14.5%<br>46.4% 6.7% 22.9% 14.5% | 6 | 0.49 |
| 7 | IF | $-N\bigcirc$ (piperidino) | 2HCl H₂O | Calc. Found | 47.9% 6.0% 22.4% 14.1%<br>47.6% 6.3% 22.2% 13.9% | 6 | 0.53 |
| 8 | IG | $-N\bigcirc$ (pyrrolidino) | 2HCl H₂O | Calc. Found | 46.8% 5.8% 23.0% 14.6%<br>47.4% 6.1% 23.3% 14.7% | 6 | 0.41 |
| 9 | IH | $-N\begin{smallmatrix}H\\i\text{-Prop}\end{smallmatrix}$ | 2HCl H₂O | Calc. Found | 43.8% 6.1% 22.7% 14.4%<br>43.3% 6.0% 22.5% 14.4% | 1 | 0.47 |
| 10 | IJ | $-N\begin{smallmatrix}H\\n\text{-But}\end{smallmatrix}$ | 2HCl H₂O | Calc. Found | 46.6% 6.2% 22.9% 14.5%<br>47.1% 6.4% 23.3% 14.6% | 2 | 0.45 |
| 11 | IK | $-N\begin{smallmatrix}i\text{-Prop}\\i\text{-Prop}\end{smallmatrix}$ | 2HCl H₂O | Calc. Found | 48.7% 6.6% 21.7% 13.7%<br>49.3% 7.0% 22.0% 13.5% | 2 | 0.47 |
| 12 | IL | $-N\begin{smallmatrix}n\text{-Bu}\\n\text{-Bu}\end{smallmatrix}$ | 2HCl H₂O | Calc. Found | 50.6% 7.0% 20.5% 13.0%<br>49.7% 6.8% 20.4% 12.7% | 3 | 0.47 |

TABLE 1-continued

| Example No. | Pteridine compound Designation | $-N\begin{matrix}R_1\\R_2\end{matrix}$ | Form of salt | | C | Elementary analysis H | N | Cl | Solvent No. | $R_f$ |
|---|---|---|---|---|---|---|---|---|---|---|
| 13 | IM | $-N\begin{matrix}H\\H\end{matrix}$ | 2HCl H$_2$O | Calc. Found | 41.6% 42.7% | 5.1% 5.3% | 25.9% 26.1% | 16.4% 16.5% | 5 | 0.41 |
| 14 | IN | $-N\begin{matrix}H\\CH_2C_6H_5\end{matrix}$ | 2HCl H$_2$O | Calc. Found | 50.5% 50.7% | 5.4% 5.2% | 21.4% 21.4% | 13.6% 13.3% | 3 | 0.37 |
| 15 | IO | $-N\underset{\smile}{\frown}N-CH_3$ | 2HCl H$_2$O | Calc. Found | 43.5% 44.0% | 5.8% 6.5% | 22.8% 23.1% | 19.2% 19.2% | 4 | 0.48 |

EXAMPLE 2

Purification of 2,4,7-triamino-6-[4-(2-hydroxy-3-dimethylaminopropoxy)phenyl-pteridine and Preparation of the Dihydrochloride Monohydrate 15.0 g of 2,4,7-triamino-6-[4-(2-hydroxy-3-dimethylaminopropoxy)phenyl]-pteridine were heated to boiling with 675 ml of 1 N hydrochloric acid in a 1-liter round-bottom flask equipped with condenser, dome heater, and magnetic stirrer. 5.0 g of activated carbon were added to the brown, clear solution nd the mixture was stirred for 15 minutes at the boiling point. The activated carbon was filtered off through a pleated filter and the solution was again heated to boiling and then passed through a membrane filter (0.2 micron, glass fiber prefilter). The solution was allowed to cool overnight to room temperature with exclusion of light. A light yellow precipitate formed. The precipitate was filtered off by suction, washed with two 20 ml portions of water with three 50 ml portions of acetone, and twice with 50 ml portions of diethyl ether, and then dried in a vacuum oven (oil-pump vacuum) for 10 hours at 60° C. and 5 hour at 105° C.

Yield: 11.95 g (64.0% of theory, calculated as dihydrochloride monohydrate). Elementary analysis:

|  | C | H | N | Cl |
|---|---|---|---|---|
| Calculated | 44.3% | 5.7% | 24.3% | 15.4% |
| Found | 44.1% | 6.0% | 24.2% | 15.5% |

The purification of the other compounds of the invention and their conversion to the hydrochlorides can be carried out by the same procedure used in Example 2.

EXAMPLE 16

Preparation of 1-(4-cyanomethylphenoxy)-3-dimethylamino-2-propanol

Reaction mixture: 10.0 g (52.9 millimoles) of 3-(4-cyanomethylphenoxy) propylene oxide (CPO), 29.8 g (264.5 millimoles) of 40% aqueous dimethylamine solution, and 100 ml methanol.

10.0 g of 3-(4-cyanomethylphenoxy)propylene oxide were dissolved in 100 ml methanol in a 250-ml round-bottom three-necked flask equipped with dropping funnel, thermometer, and magnetic stirrer.

29.8 g of 40% dimethylamine solution were slowly (over 20 minutes) added to the solution. The mixture was stirred overnight at room temperature. The methanol and excess dimethylamine were removed with a rotary evaporator and the remaining oil was taken up in 75 ml of 1 N hydrochloric acid. The solutin was extracted with three 50 ml portions of dichloromethane. The clear aqueous phase was separated and mixed with 20 ml of caustic soda solution. The aqueous phase became turbid and an oil separated. To improve separation of the oil, 30 g of common salt were added. The alkaline mixture was extracted by shaking once with 100 ml and twice with 50 ml portions of dichloromethane. The organic phases were combined and dried over sodium sulfate. After the sodium sulfate had been filtered off, the dichloromethane was removed with a rotary evaporator.

Yield: 3.0 g (70.5% of theory).

Further substituted benzyl cyanides can be prepared by the same procedure. (See Table 2.)

EXAMPLE 17

Preparation of 1-(4-cyanomethylphenoxy)-3-diisopropylamino -2-propanol

Reaction mixture: 30.0 g, (158.6 millimoles) of 3-(4-cyanomethylphenoxy)propylene oxide and 210.6 ml, (1.58 moles) of diisopropylamine.

30.0 g of 3-(4-yanomethylphenoxy)propylene oxide were refluxed with 210.6 ml diisopropylamine for 24 hours in a 500-ml round-bottom three-necked flask equipped with condenser, drying tube (with CaCl$_2$ filling), and thermometer. The white precipitate which formed during the reaction was drawn off and discarded after the batch had been cooled to room temperature. The clear filtrate was concentrated in a rotary evaporator. The residue was dissolved in 90 ml of 32% hydrochloric acid. The solution was extracted five times with 100 ml portions of dichloromethane. The organic phases were discarded. The aqueous, hydrochloric acid phase was slowly mixed with about 80 ml of 40% caustic soda solution and extracted by shaking three times with 100 ml portions of dichloromethane. Tee combined organic phases were dried over sodium sulfate. The desiccant was then filtered off and the dichloromethane was removed with a rotary evaporator.

Yield: 16.1 g (35.0% of theory).

TABLE 2

| Example No. | Compound | Reaction mixture | Procedure |
|---|---|---|---|
| 19 | 1-(4-Cyanomethylphenoxy)-3-ethylamino-2-propanol | 7.1 g (37.5 millimoles) 3-(4-cyanomethylphenoxy)propylene oxide (CPO) 33.8 g (375 millimoles) 50% aqueous ethylamine solution 100 ml methanol | * |
| 20 | 1-(4-Cyanomethylphenoxy)-3-isopropylamino-2-propanol | 5.9 g (31.2 millimoles) CPO 46.1 g (312 millimoles) 40% aqueous isopropylamine solution 100 ml methanol | As in Example 19 |
| 21 | 1-(4-Cyanomethylphenoxy)-3-methylamino-2-propanol | 10.0 g (52.9 millimoles) CPO 41.0 g (529 millimoles) 40% aqueous methylamine solution 100 ml methanol | As in Example 19 |
| 22 | 1-(4-Cyanomethylphenoxy)-3-diethylamino-2-propanol | 10.0 g (52.9 millimoles) CPO 48.25 g (264.3 millimoles) 40% aqueous diethylamino solution 100 ml methanol | As in Example 16 |
| 23 | 1-(4-Cyanomethylphenoxy)-3-morpholino-2-propanol | 10.0 g (52.9 millimoles) CPO 57.6 g (264.3 millimoles 40% aqueous morpholine solution 100 ml methanol | As in Example 16 |
| 24 | 1-(4-Cyanomethylphenoxy)-3-piperidino-2-propanol | 10.0 g (52.9 millimoles) CPO 56.3 g (264.3 millimoles) 40% aqueous piperidine solution 100 ml methanol | As in Example 16 |
| 25 | 1-(4-Cyanomethylphenoxy)-3-pyrrolidino-2-propanol | 10.0 g (52.9 millimoles) CPO 43.8 g (264.3 millimoles) 40% aqueous pyrrolidine solution 100 ml methanol | As in Example 16 |
| 26 | 1-(4-Cyanomethylphenoxy)-3-n-butylamino-2-propanol | 10.0 g (52.9 millimoles) CPO 96.7 g (529 millimoles) 40% aqueous butylamine solution 100 ml methanol | As in Example 19 |

*The ethylamine was introduced into the round-bottom flask with 50 ml methanol as initial charge, and the CPO, dissolved in 50 ml methanol, was added dropwise over 20 minutes.

EXAMPLE 18

Preparation of 1-(4-cyanomethylphenoxy)-3-dibutylamino-2-propanol

Reaction mixture: 30.0 g, (158.6 millimoles) of 3-(4-cyanomethylphenoxy) propylene oxide,
133.5 ml, (793 millimoles) of dibutylamine, and
300 ml, of methanol.

30 g. of 3-(4-cyanomethylphenoxy)propylene oxide were mixed with 133.5 ml dibutylamine and 300 ml methanol and stirred at room temperature for 20 hours. The mixture was concentrated in a rotary evaporator and the residue was taken up in 225 ml of 1 N hydrochloric acid. The acidic solution was extracted with a total of 300 ml of dichloromethane. The dichloromethane phase was discarded. The aqueous phase was mixed with about 70 ml of 4 N caustic soda solution and extracted by shaking with 200 ml dichloromethane. The dichloromethane phase was dried over sodium sulfate. The desiccant was filtered off and the dichloromethane was drawn off with a rotary evaporator.

Yield: 16.9 g (35.2% of theory).

EXAMPLE 27

Preparation of 3-(4-cyanomethylphenoxy)propylene oxide

Reaction mixture: 16.2 g, (705 millimoles) of sodium,
93.9 g, (703 millimoles) of 4-hydroxybenzyl cyanide,
250 ml, (3188 millimoles, 295 g) of epichlorohydrin
1 liter, of dimethylformamide (DMF), and
2 liters of absolute ethanol.

16.2 g of sodium were dissolved in 1 liter of absolute ethanol in a 2-liter round bottom flask. A solution of 93.9 g of 4-hydroxybenzyl cyanide in 1 liter of absolute ethanol was then added and the mixture was thoroughly stirred. The clear solution was evaporated to dryness in a rotary evaporator (bath temperature, 40° C.; first water jet, then oil pump vacuum). The red brown residue was dried in an oil pump aacuum over $P_4O_{10}$. The dry phenolate was dissolved in 1 liter of DMF. After about 100 ml of DMF had been distilled off in a rotary evaporator (bath temperature, 50° C.; oil pump), 250 ml of epichlorohydrin were added. The initially clear reaction mixture was heated to 100° C. over a period of 3 hours in an oil bath. The course of the reaction was so monitored (solvent: Ether/methanol, 95:5). The precipitated salt was separated by means of a D-4 glass filter and washed with about 200 ml of DMF. The combined filtrates were evaporated in vacuo (bath temperature, 70° C.; oil pump). The brown oil which remained was reacted further without purification.

Yield: 134 g (100% of theory).

Production of oral dosage unit forms (a) Production of granules incorporating the active ingredient 46.3 percent by weight of active substance of the invention,
78.28 percent by weight of lactose granules,
6.72 percent by weight of corn starch,
5.00 percent by weight of talc,
5.00 percent by weight of calcium carboxymethylcellulose,
0.50 percent by weight of magnesium stearate, and
0.45 percent by weight of "Aerosil", are mixed and granulated together.

(b) Production of a lactose granulation

A granulation consisting of 98 percent by weight of lactose and 2 percent by weight of a coating copolymer are produced in a fluid bed mixer from 98 kg lactose (DIN 20) with 24 kg isopropanol and 16 kg of a dimethylaminoethyl methacrylate/butyl methacrylate/methyl methacrylate (50:30:20) copolymer.

(c) Production of tablet composition

The granules of (a) incorporating the active ingredient are mixed in a tumbling mixer with the lactose-containing granules according to (b) together with 5 percent by weight of talc, 5 percent by weight of calcium carboxymethylcellulose, 6.72 percent by weight of corn starch, 0.5 percent by weight of magnesium stearate, and 0.02 percent by weight of "Aerosil". The composition is then compressed into tablets. The finished tablet contains about 2 percent by weight of the active ingredient.

Production of a capsule-filling composition 4.45 percent by weight of active compound are mixed in a tumbling mixer with 51.05 percent by weight of lactose, 42.5 percent by weight of corn starch, and 2 percent by weight of talc. The composition is then filled into hard gelatin capsules.

Production of an oral dosage unit form with Verapamil (a) Production of Verapamil granulation Verapamil is conventionally wet granulated with polyvinylpyrrolidone. The granulation is composed of 96.5 percent by weight of Verapamil and 3.5 percent by weight of polyvinylpyrrolidone.

(b) 69.45 percent by weight of active substance of the invention, 22.74 percent by weight of lactose, 5.8 percent by weight of corn starch, 0.25 percent by weight of "Aerosil", and 1.76 percent by weight of polyvinylpyrrolidone as a solution in a 1:1 mixture of isopropanol and distilled water are mixed and granulated together.

Production of tablet composition

The Verapamil-containing granulation according to (a) and the ganulation according to (b) incorporating the active substance are mixed together with 17.3 percent by weight of lactose, 7.9 percent by weight of corn starch, 5 percent by weight of calcium carboxymethylcellulose, 3.2 percent by weight of talc, 0.6 percent by weight of magnesium stearate, and 0.1 percent by weight of "Aerosil". The composition is then compressed into tablets.

The finished tablets contain the active substance of formula and Verapamil in a weight ratio ranging from 0.01:1 to 10:1.

Production of a solution of the active substance for injection (a) From the active substance alone 0.5% (g/v) of active substance of the invention is dissolved in water "for injection purpsses" (European Pharmacopoeia, vol. 2) together with an amount of sodium chloride sufficientfor isotonization. The solution is filtered to remove suspended matter and filled into ampules which are then closed and sterilized.

(b) With furosemide 0.5% (g/v) of active substanee of the invention and 2% (g/v) of furosemide are dissolved in 20% (g/v) of 1,2-propanediol and made up with water "for injection purposes" to the final volume. The solution is then handled as under (a).

Diuresis test with furosemide: Procedure For the test male Wistar rats of about 130 g body weight from which food had been with/held for 18 hours were used. They were orally given 20 ml/kg of an 0.9% NaCl solution just before the test substance was administered intravenously. Intravenous adinistration was at dosages of 8.27 mg furosemide per Kilogramm each time and compound IA at dosage intervals of 0.925 mg and of 1.85 mg per Kilogram of body weight. Injection was into the caudal vein under light ether anasthesia. As a rule six test animals were used per test. The animals were individually placed into diuresis cages and the urine was collected after 1.5 hours. Analysis was performed as for the determination of potency given above. The results are given in the following TABLE as average mean values. IA stands for 2,4,7-triamino-6-[4-(2-hydroxy-3-dimethylaminopropoxy)phenyl]-pteridine.

TABLE

| Active substance | Volume of urine [ml · kg$^{-1}$] | Na$^+$excretion [mmol · kg$^{-1}$] | K$^+$excretion [mmol · kg$^{-1}$] | Ca$^{2+}$excretion [mmol · kg$^{-1}$] | Mg$^{2+}$excretion [mmol · kg$^{-1}$] |
| --- | --- | --- | --- | --- | --- |
| None/Control | 5.0 | 0.61 | 0.33 | 0.07 | 0.08 |
| Furosemide 8.27 mg · kg$^{-1}$ | 52.5 | 6.77 | 0.68 | 0.13 | 0.11 |
| Furosemide 8.27 mg kg$^{-1}$ plus Compound IA 0.925 mg kg$^{-1}$ | 52.6 | 7.45 | 0.37 | 0.12 | 0.10 |
| Furosemide 8.27 mg kg$^{-1}$ plus Compound IA 1.85 mg kg$^{-1}$ | 51.7 | 7.15 | 0.22 | 0.12 | 0.09 |

Diuresis test with individual pteridine compounds as listed in examples 1, 3, 4, 5, 6, 7, 8, 9, 10, 11, 12: The same procedure was used as for furosemide whereby each individual pteridine compound was administered intravenously at a dosage of 2.5 μmol per Kilogramm body weight, except that the urine was collected after 2.5 hours.

| Active substance | Volume of urine [ml · kg$^{-1}$] | Na$^+$-excretion [mmol · kg$^{-1}$] | K$^+$-excretion [mmol · kg$^{-1}$] |
| --- | --- | --- | --- |
| control | 7.37 | 0.83 | 0.609 |
| triamterene (2.5 μmol) | 7.96 | 1.17 | 0.402 |
| IA (2.5 μmol) | 15.98 | 2.78 | 0.180 |
| IB (2.5 μmol) | 18.78 | 2.98 | 0.161 |
| IC (2.5 μmol) | 15.85 | 2.63 | 0.211 |
| ID (2.5 μmol) | 19.30 | 2.78 | 0.237 |
| IE (2.5 μmol) | 11.02 | 2.61 | 0.163 |
| IF (2.5 μmol) | 10.17 | 1.95 | 0.191 |
| IG (2.5 μmol) | 13.30 | 2.14 | 0.172 |
| IH (2.5 μmol) | 14.74 | 2.49 | 0.161 |
| IJ (2.5 μmol) | 18.59 | 2.86 | 0.176 |
| IK (2.5 μmol) | 10.24 | 2.08 | 0.191 |
| IL (2.5 μmol) | 13.76 | 2.34 | 0.191 |

What is claimed:

1. A pteridine compound of the formula

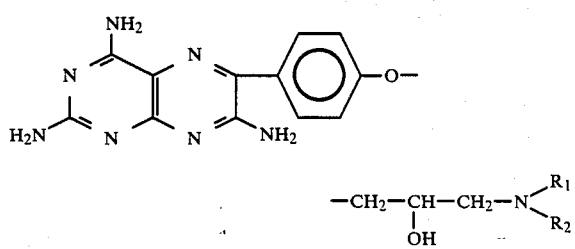

or a pharmaceutically acceptable acid addition salt thereof, wherein one of $R_1$ or $R_2$ is benzyl and the other is hydrogen, alkyl having from 1 to 6 carbon atoms, or benzyl, or wherein $R_1$ and $R_2$, taken together with the nitrogen atom to which they are bound, form a pyrrolidinyl, piperidinyl, morpholinyl, piperazinyl, or N'-alkyl piperazinyl group, or wherein $R_1$ and $R_2$ together with the nitrogen are

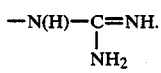

2. A compound as in claim 1 which is 2,4,7-triamino-6-[4-[2-hydroxy-3-(morpholin-4-yl)-propoxy]-phenyl]-pteridine or an acid addition salt thereof.

3. A compound as in claim 1 which is 2,4,7-triamino-6-[4-[2-hydroxy-3-(piperidin-1-yl)-propoxy]-phenyl]-pteridine or an acid addition salt thereof.

4. A compound as in claim 1 which is 2,4,7-triamino-6-[4-[2-hydroxy-3(pyrrolidin-1-yl)-propoxy]-phenyl-]-pteridine or an acid addition salt thereof.

5. A compound as in claim 1 which is 2,4,7-triamino-6-[4-[2-hydroxy-3(4-methyl-piperazin-1-yl)propoxy]-phenyl]-pteridine or an acid addition salt thereof.

6. A compound as in claim 1 which is 2,4,7-triamino-6-[4-(2-hydroxy-3-benzylaminopropoxy)-phenyl]pteridine or an acid addition salt thereof.

7. A diuretic-antikaluretic-antihypertensive pharmaceutical preparation comprising a compound or salt as in claim 1 and a pharmaceutically acceptable carrier therefor.

8. A pharmaceutical preparation as in claim 7 comprising a daily dose from 0.2 to 100 mg of the active substance.

9. A diuretic-antikaluretic-antihypertensive pharmaceutical composition in dosage unit form for oral administration comprising an effective amount of a compound or salt as in claim 1 and an orally ingestible pharmaceutical excipient therefor.

10. A diuretic-antikaluretic-antihypertensive pharmaceutical composition in dosage unit form for parenteral administration comprising an effective amount of a compound or salt as in claim 1 and an injectable pharmaceutical excipient therefor.

11. A method for inducing diuresis in a patient, which method comprises orally or parenterally administering to said patient a diuretically effective amount of a compound or salt as in claim 1.

* * * * *